(12) United States Patent
Bojovic et al.

(10) Patent No.: US 7,647,093 B2
(45) Date of Patent: Jan. 12, 2010

(54) APPARATUS AND METHOD FOR CORDLESS RECORDING AND TELECOMMUNICATION TRANSMISSION OF THREE SPECIAL ECG LEADS AND THEIR PROCESSING

(75) Inventors: Bosco Bojovic, Beograd (YU); Ljupco Hadzievski, Beograd (YU); Petar Belicev, Beograd (YU)

(73) Assignee: New Cardio, Inc., San Jose, CA (US)

( * ) Notice: Subject to any disclaimer, the term of this patent is extended or adjusted under 35 U.S.C. 154(b) by 381 days.

(21) Appl. No.: 10/568,868

(22) PCT Filed: Aug. 19, 2004

(86) PCT No.: PCT/YU2004/000020

§ 371 (c)(1),
(2), (4) Date: Feb. 21, 2006

(87) PCT Pub. No.: WO2005/018447

PCT Pub. Date: Mar. 3, 2005

(65) Prior Publication Data

US 2006/0217620 A1  Sep. 28, 2006

(30) Foreign Application Priority Data

Aug. 20, 2003  (YU) .................................... 656/03

(51) Int. Cl.
*A61B 5/0402* (2006.01)
(52) U.S. Cl. ...................... 600/509; 600/512
(58) Field of Classification Search ........... 600/508, 600/509, 512, 520, 522, 523, 525
See application file for complete search history.

(56) References Cited

U.S. PATENT DOCUMENTS

| 3,848,582 | A | * | 11/1974 | Milani et al. | ............... 600/372 |
| 4,270,547 | A | | 6/1981 | Rinard | |
| 4,513,753 | A | | 4/1985 | Sawada | |
| 4,535,783 | A | * | 8/1985 | Marangoni | ............... 600/524 |

(Continued)

FOREIGN PATENT DOCUMENTS

WO  WO/89/00024 A  1/1989

(Continued)

*Primary Examiner*—Scott M Getzow
(74) *Attorney, Agent, or Firm*—Nixon Peabody LLP

(57) ABSTRACT

The invention is related to a device and method for cordless recording, telecommunication transmission, and processing of three special ECG leads by the means of the mobile device (1) and diagnostic-calibration center (2) where the reconstruction of standard ECG leads is performed. Reconstruction parameters are determined previously by calibration for each patient. In urgent situation, a patient (3) performs recording of three special ECG leads with the mobile device (1), and sends the memorized data to the diagnostic-calibration device (2) via a cellular telephone (4). The patient can trace the process of recording and sending the data with the help of sound and light indicators. Diagnostic-calibration center (2) is equipped with a PC computer (6) connected to a receiving cellular telephone (7) and calibration ECG device (8) with 14 electrodes. Ten electrodes are grouped into a standard 12-channel ECG cable, while the remaining four are used for recording of three special ECG leads and are grouped into a separate box (9) with integrated electrodes arranged identically as the integrated electrodes on the mobile device (1).

33 Claims, 2 Drawing Sheets

U.S. PATENT DOCUMENTS 4,938,228 A    7/1990  Righter
5,704,351 A *  1/1998  Mortara et al. .............. 600/382
5,876,351 A    3/1999  Rhode
6,654,631 B1 * 11/2003 Sahai ......................... 600/509

FOREIGN PATENT DOCUMENTS

WO    WO/01/70105 A    9/2001

* cited by examiner

APPARATUS AND METHOD FOR CORDLESS RECORDING AND TELECOMMUNICATION TRANSMISSION OF THREE SPECIAL ECG LEADS AND THEIR PROCESSING

TECHNICAL FIELD

The present invention is related to the field of medical electronics, more precisely to the field of instruments for measuring and recording bioelectric signals, such as electrocardiographs. It concerns devices for data acquisition, processing, and transmission via commercial telecommunication network. According to the International Patent Classification (IPC), the invention is categorized within the A61B 5/00 class, which defines methods or devices for measurement or recording in diagnostics purposes. More specifically, the invention is categorized within the A61B 5/04 class, which defines instruments for measuring or recording bioelectric charges of a body or an organ, such as electrocardiographs.

TECHNICAL PROBLEM

The invention resolves the construction problem of the device and procedure for cordless recording, telecommunication transmission, and processing of three special ECG leads. It implies the use of a mobile pocket device with integrated electrodes, three of which are connected to the active inputs of the amplifier coupled to the control module, one of which is passive, and one connected to the ground. The invention, with precisely defined procedure for recording, transmission and processing, enables quick, simple, and accurate cordless self-recording (by the patient himself) with the device, transmission of three ECG leads, and obtaining of standard 12-lead ECG recording. During this process, the 12-lead ECG recording will be reconstructed with the satisfying accuracy, and the possibility for an error due to the incorrect positioning of the electrodes will be excluded as well as the possibility for a major diagnostic error due to so called base line wandering of the ECG signal during recording. Thus, the application of the device will be enabled within the widest spectrum of heart diseases with diagnoses of cardiac ischemia (Coronary Artery Disease—CAD).

BACKGROUND ART

The concept of the system for urgent cardiac diagnostics which enables a patient, wherever he may be, to record his ECG himself and send it to his cardiologist in the remote diagnostic center via commercial telecommunication network (cellular or fixed telephone line) is well known. Namely, on the bases of the received ECG and the conversation with the patient, the cardiologist on duty can decide: a) whether an urgent intervention is needed, b) whether the intervention can be performed by the patient himself, or c) whether the patient's state requires urgent medical intervention, and acts accordingly. It is very important that the most critical period, from the occurrence of the first symptoms until the medical treatment, be minimized (Lenfant C. et al.: Considerations for a national heart attack alert program, Clin. Cardiol. 1990 August; 13 (8 Suppl 8): VIII9-11). There is a number of patents and products which, within the said concept of urgent cardiological diagnostics, offer different solutions for recording and transmitting the ECG signal: U.S. Pat. No. 4,889,134 Greenwold, et al., 1989; U.S. Pat. No. 5,226,431 Bible, et al. 1993; U.S. Pat. No. 5,321,618 Gessman, 1994; U.S. Pat. No. 5,966,692 Langer, et al., 1999; PCT WO 01/70105 A2, B. Bojović 2001; "Instant Memory Recorder" of the company TELESCAN MEDICAL SYSTEMS (TELESCAN MEDICAL SYSTEMS 26424 Table Meadow Road, Auburn, Calif. 9560); "CardioCall Event Recorder" by REYNOLDS MEDICAL (REYNOLDS MEDICAL LTD, John Tate Road, Hertford SG13 7NW United Kingdom) and "Heartwiev P-12" by AEROTEL (AEROTEL LTD. 5 Hazoref st. Holon 58856 Israel). The solutions can be divided into three groups:

1) The first group comprises solutions for sending the recording of one or two standard ECG leads. The mobile recorders of this group can be very small and with integrated electrodes (no cables are needed), which is the advantage of the group. The recording is performed by simple holding of the device on the patient's chest or by positioning the fingers on the integrated electrodes. This is a quick and simple way for a patient to record one or two leads of his ECG. However, recording one or two ECG signals limits the application of these devices to the patients with rhythm disorders, which is about 20% of the patient population with heart diseases. Typical device of this group is "CardioCall Event Recorder" by REYNOLDS MEDICAL.

2) The second group consists of solutions that enable direct recording and transmission of standard 12-lead ECG, thus including their application to the patients with the diagnoses of coronary artery diseases. Namely, in such patients, the complete standard 12-lead ECG is necessary for urgent diagnostics. Some of these devices are equipped with the full set of electrodes and cables for recording all 12 standard ECG leads (usually 10 electrodes, that is cables), which a patient himself attaches onto his body during recording. The typical representative of this group is "12 Lead Memory ECG Recorder" by TELESCAN MEDICAL SYSTEMS. The other method is the use of a reduced number of electrodes that are moved during the recording. For example, if four electrodes are used, three are positioned at the locations of standard ECG leads I, II, and III (arms and legs of the patient), while the fourth electrode has to be moved during recording to each of the six chest positions for recording chest leads V1-V6 (U.S. Pat. No. 4,889,134, Greenwold et al., 1989). The method that uses three cable connected electrodes and four button-shaped integrated electrodes can be found in the device "Heartwiev P-12" by AEROTEL. The recording of 12 leads is performed in three steps: leads D1, D2, D3, aVR, aVL, aVF, V1, and V2 are recorded in the first step, V3 and V4 in the second, and V5 and V6 in the third step. The common disadvantage of the whole group is rather complicated and long-lasting recording procedure, which makes them very inconvenient for self-application, especially for the patients suffering a heart attack. Significant errors are also possible to occur due to the imprecise positioning of the electrodes.

3) The third group includes the solutions in which reduced number of special leads is recorded, and later, on the basis of this recording, all 12 standard ECG leads are reconstructed computationally. The method for the reconstruction of 12 standard ECG leads and/or x,y,z leads of a vectorcardiogram based on the recorded special leads obtained with four electrodes is explained in U.S. Pat. No. 4,850,370, G. E. Dower 1989. The method is based on the dipole approximation of the electrical heart activity and uses the universal transformation matrix T, with dimensions 3×12, and with the matrix coefficients determined experimentally.

The conventional ECG leads $\vec{t}(D_1, D_2, D_3, aVR, aVL, aVF, V_1, V_2, V_3, V_4, V_5, V_6)$ are obtained by multiplying the transformation matrix T with the recorded signals at the special leads $\vec{t}_s(V_{s1}, V_{s2}, V_{s3})$. The universal transformation matrix for all patients does not contain information about individual characteristics of a patient, which results in major errors in the reconstruction of the standard ECG lead signals.

An improvement of this method by introducing the individual transformation matrix is given in the paper by Scherer, J. A. et al., Journal of Electrocardiology, v 22 Suppl, pp. 128, 1989, and applied in the U.S. Pat. No. 5,058,598 (J. M. Niklas et al., 1993), where the implementation of the individual transformation matrix for each patient, with the segment calculation of the transformation matrix coefficients, was suggested (ECG signal is divided into segments and the coefficients for each segment are calculated individually). The reconstruction of the standard ECG lead signals by the individual transformation matrix means that it is necessary to perform the basic (calibrating) recording for each patient, which will be used for the matrix coefficient calculation. The errors in this approach are significantly reduced compared to the method using the universal transformation matrix. The major drawback of both said methods is the need to use cables for recording with the suggested arrangement of electrodes which is very inconvenient for self-application, especially in the patients suffering a heart attack. The method in which the reconstruction of standard ECG leads is also done with the individual transformation matrix (Scherer, J. A. et al., Journal of Electrocardiology, v 22 Suppl, pp. 128, 1989), but with the mobile ECG device with integrated electrodes, i.e. with no cables used, is presented in the patent PCT WO 01/70105 A2, B. Bojović 2001. The device enables quick and easy recording of the special ECG leads and reconstruction of all 12 standard ECG leads with the individual transformation matrix. However, the limitations in the arrangement of the electrodes, due to the use of the integrated ones, disable the optimal arrangement of electrodes on the patient's body, which results in significant errors in the signal reconstruction.

An additional problem present in all three groups is the occurrence of the base line wandering of the ECG signal during recording. The effect is especially undesirable for the third group of the said devices because the base line wandering during the recording of special leads brings about major diagnostic errors in the procedure of the reconstruction of 12 standard ECG leads.

DISCLOSURE OF INVENTION

The invention presents the method and device for cordless recording, telecommunication transmission, and processing of three special ECG leads. The recording of three special ECG leads is performed with the mobile device with strictly defined arrangement of integrated electrodes and the way of recording, which, after the transmission to a remote PC computer, enables the precise reconstruction of all 12 signals of standard ECG leads. In this way, the simplicity of use of the device with integrated electrodes is combined with high recording accuracy, until now possible only with the devices using cables for recording. The system consists of the stationary diagnostic callibration center and the mobile ECG device with integrated electrodes. The diagnostic callibration center comprises a PC computer with the corresponding software, connected to a cellular telephone and a callibration ECG device with 14 electrodes. The calibration device is used for simultaneous recording of patient's 12 standard and three special ECG leads. The recording of special leads is performed in a way which a patient will use himself while recording with the mobile ECG device with integrated electrodes. On the basis of the recorded data the transformation matrix of a patient is calculated and stored into a database. The obtained matrix is used for calculation of 12 standard ECG leads every time the patient sends, via telephone, the recording of three special leads taken by himself using the mobile ECG device with integrated electrodes.

The accuracy in the reconstruction of 12 standard ECG leads using the recordings of three special leads is achieved by strictly defined arrangement of integrated electrodes in the mobile device and by the special way of recording. The reconstruction algorithm is based on the assumption that diffused electrical activity of the heart muscle can be approximated by a time-changing electrical dipole (heart dipole) immersed in a low conducting environment. Heart dipole is a vector defined by three non-coplanar projections, so that it can be determined on the basis of recording of electric potential in any three points corresponding to three non-coplanar directions, i.e. three ECG leads not laying on the same plane. Once the heart vector is determined, it is easy to calculate the electric potentials in any point, meaning the 12 standard ECG leads as well. The calculation of heart dipole is not necessary; the direct connection between the recorded special leads and standard ECG leads can be established instead, so that standard ECG leads are obtained as linear combinations of the recorded special leads and coefficients by which the transformation matrix is defined. However, direct application of this approach with no detailed analysis of the error sources and their reduction gives rather poor reconstruction results. The analysis has shown that there are two dominant error sources that should be taken into consideration.

a) Model Errors

The system of reconstruction of the standard ECG leads on the basis of recording of three special leads is based on the dipole representation of heart electrical activity. However, the heart dipole is only the first term in the multipole expansion of diffused heart electrical activity and this approximation is valid only for recording points at the sufficient distance from the heart. In the points near the heart, the potential is significantly affected by the non-dipole content created due to the presence of higher order terms in multipole expansion.

b) Transformation Matrix Calculation Errors

Practical calculation of transformation matrix T is done by the simultaneous recording of 12 standard ECG leads $\vec{r}(D_1, D_2, D_3, aVR, aVL, aVF, V_1, V_2, V_3, V_4, V_5, V_6)$ and three special leads $\vec{r}_s(V_{s1}, V_{s2}, V_{s3})$, followed by numerical solving of the equation $\vec{r} = T \cdot \vec{r}_s$ by the least-squares method. The errors in recording the electric potentials introduce the errors in the calculation of transformation matrix coefficients. The analysis has shown that the errors would be minimized if the vectors of special leads recording points were orthogonal.

Finally, having in mind the model errors (a) and the transformation matrix calculation errors (b), two requirements are imposed concerning the arrangement of the integrated electrodes for special leads recording, in order to minimize the total error. The first one is to position the electrodes of the special leads as far as possible from the heart; the second one is to arrange the electrodes in such a way that the vectors of recording points' positions are close to orthogonal as much as possible. Both said conditions cannot be fulfilled simultaneously when recording of the special leads should be performed with the mobile ECG device with integrated electrodes, i.e. without cables. The solution we offer presents the optimal configuration fulfilling the said requirements to the furthest extent within the limitations imposed by the use of the mobile ECG device with integrated electrodes. The mobile ECG device is designed in such a way that two integrated electrodes could be touched with the fingers of the left and right hand, while two electrodes are simultaneously in contact with the patient's chest. The patient's hands are used as flexible elements for moving two recording points away from the heart (as the source of the electrical activity), using the electrode in contact with a finger of the right hand as the reference point for the recording of all three special leads. The electrodes in electrical contact with the patient's chest are set in the precisely defined position within the limited area on the patient's chest. By arranging the electrodes positions in this way, and choosing the reference point, the optimal minimization of the model errors (a) and transformation matrix calculation errors (b) has been achieved.

An additional problem in signal recording of special as well as of standard ECG leads is the effect of the base line wandering of the recorded signals. The problem occurs during the recording of ECG signals with all kinds of ECG devices, but is more prominent with mobile ECG devices due to the more difficult recording conditions, especially with the devices intended for patient's recording of his own ECG. When systems which obtain standard ECG leads by the reconstruction of recorded special leads are concerned, the elimination of the base line wandering problem during recording of special leads is extremely important for the proper functioning of the system. This invention establishes the control of the base line wandering during recording of special leads with a mobile ECG device with integrated electrodes by the means of digital control module which controls and manages the process of recording automatically. From the moment of putting the device into the recording position until the moment when the base line of a signal fits into the previously specified range, a characteristic sound signal is being emitted. During the next period defined by the signal relaxation time, another characteristic sound signal is being emitted, informing a patient that the recording will start soon. The recording itself is indicated by the third characteristic sound signal. If the significant base line wandering occurs in any phase of the procedure, the procedure will be repeated from the beginning. Doing so, the patient is enabled to send the high-quality recording of special leads, which makes possible the accurate reconstruction of standard ECG leads.

The arrangement of integrated electrodes described above, their positioning, the way of recording, and described system for eliminating the base line wandering of recorded signals minimize the errors in the reconstruction of standard ECG leads, making the accuracy of recording similar to the standard ECG devices. Thus, the simplicity in use of the device with integrated electrodes is combined with high precision of the devices using cables for recording.

DETAILED DESCRIPTION OF INVENTION

Figure 1:
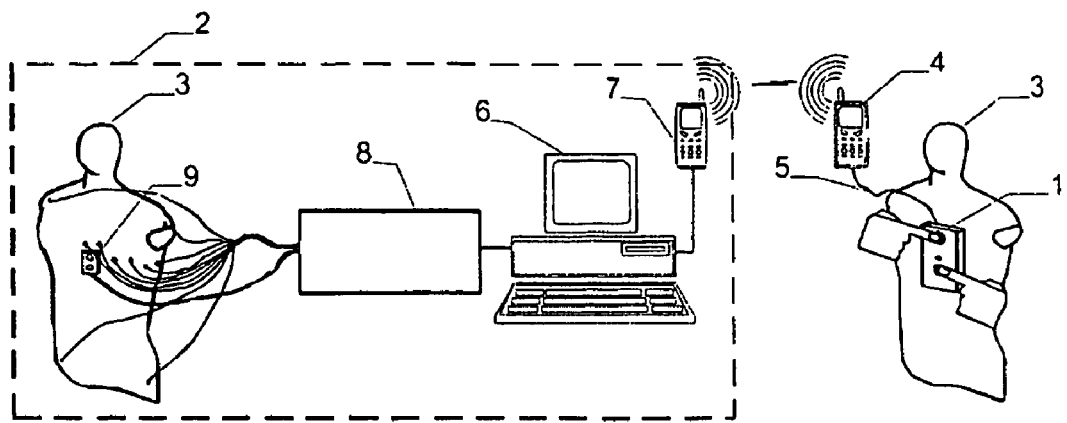
FIG. 1—Schematic representation of the device for cordless recording, telecommunication transmission, and processing of three special ECG leads FIG. 2—Schematic representation of the arrangements of the integrated electrodes on the mobile ECG device FIG. 3—Positioning of a mobile ECG device onto the patient's chest and the recording procedure FIG. 4—Isometric view of a mobile ECG device with integrated electrodes FIG. 5—Block diagram of the electric scheme of the mobile ECG device FIG. 6—Schematic representation of the positioning of a mobile ECG device, i.e. of its electrodes, onto the patient's chest.

FIG. 1 shows the scheme of a device for recording three special ECG leads with the mobile ECG device 1 and their transmission to the diagnostic-calibration center 2 where, on the basis of the received special leads, computational reconstruction of standard ECG leads is performed. In order to realize the said reconstruction, it is necessary to determine corresponding reconstruction parameters for each patient by previous calibration. Recording of three special leads in urgent situation is performed by the patient 3 with the mobile device 1. The patient sends the memorized data into the diagnostic-calibration center 2 by means of a cellular telephone 4 that is connected to the mobile device 1 with the communication cable 5. There are sound and light indicators that help the patient to monitor the process of recording and sending the data. The diagnostic-calibration center 2 is equipped with a PC computer 6 containing the suitable software, connected to the receiving cellular telephone 7 and the calibration ECG device 8 with 14 electrodes. Ten electrodes are grouped into the standard 12-lead ECG cable, while the remaining four are used for recording of three special ECG leads and are grouped into the separate box 9 with integrated electrodes arranged in the exactly same way as the electrodes in the mobile device 1. In the present embodiment, the data transmission via cellular telephones 4 and 7 is shown, but the method itself will not be changed if the data transmission is performed by fixed telephone line with the help of a modem or if cordless communication is used instead of the cable 5 for communication between the mobile device 1 and the cellular telephone 4.

During the calibration procedure, the first step comprises simultaneous recording of 12 standard and three special ECG leads with the calibration device, and in the second step, the reconstruction parameters are determined by the corresponding software on the PC computer 6. The software for calculation of parameters is based on the application of the least-squares deviation method. The reconstruction parameters are organized as a transformation matrix and they define a linear transformation between standard and special ECG leads. Transformation matrix for each patient is calculated separately and stored into a database in memory of the PC computer 6. Later, with the help of the software on the PC computer 6, this matrix is used for reconstruction of 12 standard ECG leads on the basis of three special leads recorded by the patient himself in the urgent situation and sent to the diagnostic-calibration center 2 via the cellular telephone 4. The software on the PC computer 6 enables the display of the reconstructed ECG leads on the computer monitor and/or a printer. In order to make this procedure accurate, it is necessary that the electrodes on the box 9 connected to the calibration device 8 are arranged identically as the electrodes in the mobile device 1. It is also necessary that the positions of the electrodes on the patient's body during the calibration are identical to the positions of the electrodes during the recording using the mobile device in urgent situation.

Figure 2:
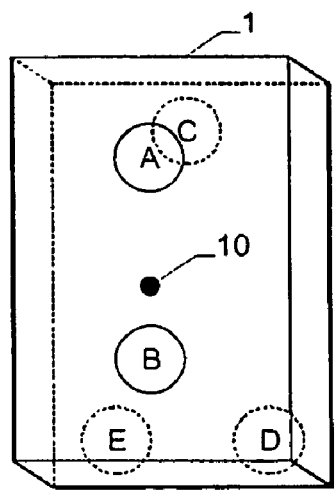

The scheme of the arrangement of integrated electrodes in the mobile ECG device 1 is given in FIG. 2. There are five integrated electrodes, two of which are located on the front side of the device (electrodes A and B), and three are on the back side of the device (electrodes C, D, and E). The push-button 10 on the front side of the device is used for activation of the recording and the process of sending the data.

Figure 3:
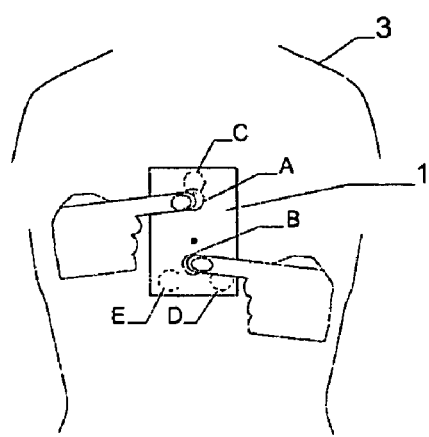

The positioning of the mobile ECG device 1 onto the chest of the patient 3 and the recording procedure are shown in FIG. 3. The device is positioned vertically onto the patient's chest so that the electrodes C, D, and E touch the patient's chest simultaneously. During recording, the device is held with a right hand finger on the electrode A, and a left hand finger on the electrode B.

Figure 4:
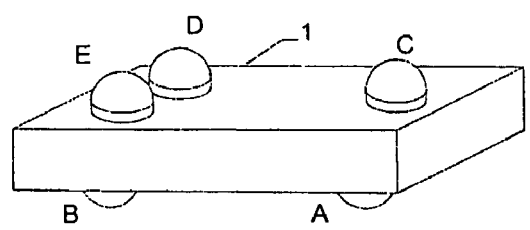

Block diagram of the electric scheme of the mobile ECG device 1 and the connection scheme of recording electrodes at the amplifier input points are given in FIG. 4. The electrical part of the device consists of the amplifier module 11 and the digital control module 12. The amplifier module 11 contains three amplifiers (111, 112, and 113) for amplifying the signals of three special leads. The electrode A, in electrical contact with the right hand, is connected in such a way that it represents the common reference point for all three amplifiers, i.e. recording leads. The electrodes B, C, and D are connected to the active recording points of the amplifiers 111, 112, and 113. The electrode E is connected to the common ground of all three amplifiers. Thus, the electrode A represents the reference (passive) point for recording the potentials of the remaining electrodes B, C, and D.

For the proper functioning of the method, it is necessary that the positions of the special leads recording points on the patient's body are the same in the calibration process and during the recording on the basis of which the reconstruction is performed. In accordance with this, it is necessary that the arrangement of electrodes on the mobile device 1, given in FIG. 2, be the same as the arrangement of electrodes on the box 9 of the calibration device. Also, it is necessary that the recording procedure shown in FIG. 3 be performed in the same way while using the mobile device 1 and while using the calibration device 8, that is, while positioning the recording electrodes of the box 9. Beside the basic arrangement (A—right hand, B—left hand, C, D, E—chest), it is important that, for the same patient, the position on the chest during the calibration is kept as close as possible to the position during recording with the mobile device in order to minimize the reconstruction errors caused by the change of the electrode positions.

The arrangement of the electrodes A and B on the front side of the device can be arbitrary, while it is necessary that they be used as presented in FIG. 3 (A—right hand, B—left hand). The position of the electrode E (common ground) can be arbitrary or its use can be avoided if the electric scheme is solved in a different way. In the case of the box 9, the common ground of the remaining amplifiers of the calibration device, which is conventionally positioned on the patient's right leg, can be used instead of the electrode E.

Figure 5:
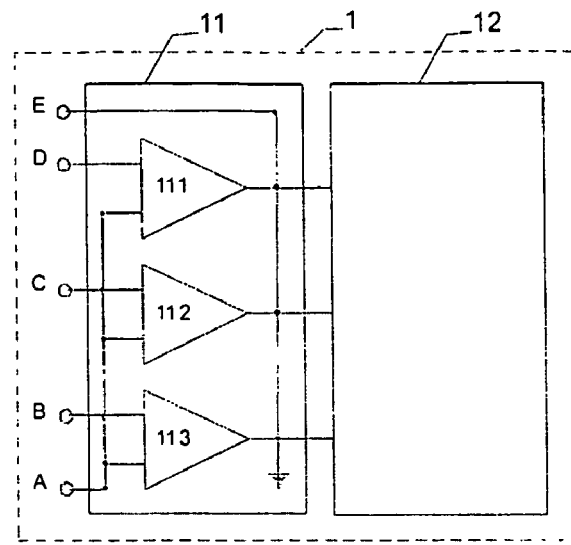
Figure 6:
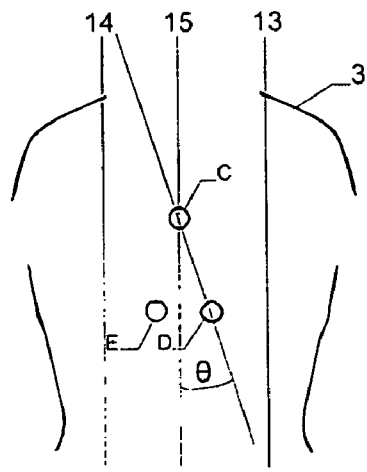

The position of the active electrodes (C and D), providing the electrical contact with the patient's chest, is vital for the proper functioning of the whole system. Illustration of the position of active electrodes is shown in FIG. 5. Active electrodes C and D are positioned onto the patient's chest in the area between the left 13 and the right 14 mamilar line (linea mamillaris). These electrodes should lie on the direction that, with the direction of the medial line (linea mediana anterior), makes the angle θ ranging from 30° to 90° (FIG. 6). The position of the electrode E, which represents the common ground, can be arbitrary, but it is convenient to choose it in such a way that it provides the mechanical stability of the mobile ECG device while in recording position, held against the patient's chest.

The operating of the amplifier module 11 of the mobile device 1 is controlled and managed with the digital control module 12. From the moment of putting the mobile device 1 in the recording position, the control module 12 checks the signal level at the output of the amplifiers 111, 112, and 113. As long as the signal level is out of the specified operating range of ±2.5 mV, the characteristic sound signal, which the patient can easily memorize, is being emitted. From the moment when the signal level fits into the said operating range, another characteristic sound signal is being emitted for the following five seconds. This signal informs the patient that the recording will start soon. This recording delay period (five seconds) is approximately determined by the time constant of the amplified signal stabilization and depends on the frequency response of the amplifier. The third characteristic sound signal indicates the recording process itself. If in any phase of the procedure described above the base line wandering occurs, the digital control module 12 detects the event and the whole procedure is repeated from the beginning. The procedure of controlling the recording process enables the patient to perform a high-quality recording of special leads, thus enabling the accurate reconstruction of standard ECG leads.

The change of the operating range of the amplifier and the recording delay time does not effect the invention itself.

The way of recording described above, electrode arrangement and their positioning, and control procedure of recording provide the conditions for highly accurate reconstruction of standard 12 ECG leads. Thus, the invention combines the simplicity in use of a device with integrated electrodes with high precision of the devices using cables for recording.

The experts in this field are familiar with the fact that small modifications of the block-scheme and procedure can be performed without exceeding the scope of the invention.

The invention claimed is:

1. A handheld device adapted for placement against the body of a patient in a measurement position to thereby extract special ECG signals for combining with a predetermined calibration matrix in order to construct an ECG, the handheld device comprising:

at least three integrated active electrodes, including first and second integrated active electrodes adapted to electrically contact the chest of the patient in the measurement position, and a third integrated active electrode adapted to electrically contact the left hand of the patient in the measurement position; and a integrated fourth electrode adapted to electrically contact the right hand of the patient in the measurement positions wherein said integrated active electrodes and integrated fourth electrode are disposed in the device such that, when in the measurement position, said contact with the chest of the patient by the first and second integrated active electrodes, with the left hand of the patient by the third integrated active electrode, and with the right hand of the patient by the integrated fourth electrode, is operative to achieve maximum recording point vector orthogonality, to thereby optimize ECG reconstruction.

2. The device of claim 1, wherein the first and second integrated active electrodes are arranged such that in the measurement position they are disposed on the patient between the right and left mamilar lines (linea mamillaris) and lie in a line transverse to the medial line (linea mediana anterior) at an angle ranging from about 30° to about 90°.

3. The device of claim 1, wherein the first and second integrated active electrodes are disposed on a first side of the handheld device and the third integrated active electrode is disposed on a side of the handheld device different from the first side.

4. The device of claim 1, wherein the first and second integrated active electrodes are disposed on a first side of the handheld device and the integrated fourth electrode is disposed on a side of the handheld device different from the first side.

5. The device of claim 1, further comprising a integrated fifth electrode arranged such that in the measurement position, the integrated fifth electrode is in electrical contact with the chest of the patient.

6. The device of claim 5, wherein the first and second integrated active electrodes and the integrated fifth electrode are all disposed on a first side of the handheld device.

7. The device of claim 5, further comprising an amplifier module including first, second and third amplifiers each having associated therewith a first input node adapted for connection to the first, second and third integrated active electrodes, respectively, a reference node adapted for connection to the integrated fourth electrode, and a ground node adapted for connection to the integrated fifth electrode.

8. The device of claim 7, further comprising a control module adapted to receive the outputs of first, second and third amplifiers of the amplifier module and to indicate whether said outputs are within or outside a predetermined range.

9. The device of claim 8, wherein the control module provides an indication of ECG recording status.

10. The device of claim 1, wherein the ECG is a standard 12-lead ECG.

11. A diagnostic system for constructing an ECG of a patient, the system comprising:
a field unit including a handheld device adapted for placement against the body of the patient in a measurement position to thereby extract special ECG signals for combining with a predetermined calibration matrix, the handheld device comprising:
at least three integrated active electrodes, including first and second integrated active electrodes adapted to electrically contact the chest of the patient in the measurement position, and a third integrated active electrode adapted to electrically contact the left hand of the patient in the measurement position; and
an integrated fourth electrode adapted to electrically contact the right hand of the patient in the measurement position wherein said integrated active electrodes and integrated fourth electrode are disposed in the device such that, when in the measurement position, said contact with the chest of the patient by the first and second integrated active electrodes, with the left hand of the patient by the third integrated active electrode, and with the right hand of the patient by the integrated fourth electrode, is operative to achieve maximum recording point vector orthogonality, to thereby optimize ECG reconstruction; and
a diagnostic center in communication with the field unit, the diagnostic center configured to receive signals derived from the three integrated active electrodes and construct therefrom, and from said predetermined calibration matrix, an ECG of the patient.

12. The system of claim 11, wherein the first and second integrated active electrodes are arranged such that in the measurement position they are disposed on the patient between the right and left mamilar lines (linea mamillaris) and lie in a line transverse to the medial line (linea mediana anterior) at an angle ranging from about 30° to about 90°.

13. The system of claim 11, wherein the first and second integrated active electrodes are disposed on a first side of the handheld device and the third integrated active electrode is disposed on a side of the handheld device different from the first side.

14. The system of claim 11, wherein the first and second integrated active electrodes are disposed on a first side of the handheld device and the integrated fourth electrode is disposed on a side of the handheld device different from the first side.

15. The system of claim 11, further comprising integrated fifth electrode arranged such that in the measurement position, the integrated fifth electrode is in electrical contact with the chest of the patient.

16. The system of claim 15, wherein the first and second integrated active electrodes and the integrated fifth electrode are all disposed on a first side of the handheld device.

17. The system of claim 15, further comprising an amplifier module including first, second and third amplifiers each having associated therewith a first input node adapted for connection to the first, second and third integrated active electrodes, respectively, a reference node adapted for connection to the integrated fourth electrode, and a ground node adapted for connection to the integrated fifth electrode.

18. The system of claim 17, further comprising a control module adapted to receive the outputs of first, second and third amplifiers of the amplifier module and to indicate whether said outputs are within or outside a predetermined range.

19. The system of claim 18, wherein the control module provides an indication of ECG recording status.

20. The system of claim 11, wherein the field unit includes a communication module adapted to communicate with the diagnostic center.

21. The system of claim 20, wherein the communication module is a cellular device.

22. The system of claim 20, wherein the communication module is a modem.

23. The system of claim 11, wherein the ECG is a standard 12-lead ECG.

24. A method for constructing a patient ECG, the method comprising:
placing against the body of the patient in a measurement position a handheld device having first, second and third integrated active electrodes and an integrated fourth electrode, wherein said integrated active electrodes and fourth integrated electrodes are disposed in the device such that, when in the measurement position, contact is with the chest of the patient by the first and second integrated active electrodes, with the left hand of the patient by the third integrated active electrode, and with the right hand of the patient by the integrated fourth electrode, and is operative to achieve maximum recording point vector orthogonality, to thereby optimize ECG reconstruction;
extracting from the first and second integrated active electrodes, respectively, first and second electrical signals derived from the chest of the patient;
extracting from the third integrated active electrode a third electrical signal derived from the left hand of the patient;
extracting from the integrated fourth electrode a reference signal derived from the right hand of the patient;
communicating signals corresponding to the extracted signals to a diagnostic center; and
combining, at the diagnostic center, the communicated signals with a predetermined calibration matrix to construct, an ECG of the patient.

25. The method of claim 24, wherein, in the measurement position, the first and second integrated active electrodes are disposed on the chest between the right and left mamilar lines (linea mamillaris) and lie in a line transverse to the medial line (linea mediana anterior) at an angle ranging from about 30° to about 90°.

26. The method of claim 24, wherein, in the measurement position, both arms of the patient are folded such that at least portions of the right and left hands of the patient establish electrical contact with the handheld device placed against the chest of the patient.

27. The method of claim 24, wherein the first and second integrated active electrodes are disposed on a first side of the handheld device and the third integrated active electrode is disposed on a side of the handheld device different from the first side.

28. The method of claim 24, wherein the first and second integrated active electrodes are disposed on a first side of the handheld device and the integrated fourth electrode is disposed on a side of the handheld device different from the first side.

29. The method of claim 24, further comprising providing an indication of whether the first, second and third electrical signals are within or outside a predetermined range.

30. The method of claim 24, further comprising providing an indication of ECU recording status.

31. The method of claim 24, wherein the ECG is a standard 12-lead ECG.

32. The method of claim 24, wherein the predetermined calibration matrix is acquired using a calibration device having an electrode arrangement and amplifiers nodes arrangement which is substantially identical to that of the handheld device.

33. The method of claim 24, wherein the predetermined calibration matrix is acquired using a calibration device in the same position on the patient's body and in a substantially identical manner as the handheld device.

* * * * *

UNITED STATES PATENT AND TRADEMARK OFFICE
CERTIFICATE OF CORRECTION

PATENT NO. : 7,647,093 B2  Page 1 of 1
APPLICATION NO. : 10/568868
DATED : January 12, 2010
INVENTOR(S) : Bojovic et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 480 days.

Signed and Sealed this

Sixteenth Day of November, 2010

David J. Kappos
*Director of the United States Patent and Trademark Office*